United States Patent [19]
Johnson et al.

[11] Patent Number: 5,769,826
[45] Date of Patent: Jun. 23, 1998

[54] SPRING LOADED RETRACTABLE CANNULA BLOOD DRAWING DEVICE

[76] Inventors: Kenneth H. Johnson; Richard L. Moseley, both of P.O. Box 630708, Houston, Tex. 77263

[21] Appl. No.: 819,568

[22] Filed: Mar. 14, 1997

[51] Int. Cl.⁶ .................................................. A61M 5/00
[52] U.S. Cl. .......................................... 604/195; 128/763
[58] Field of Search .................................... 604/195, 198, 604/192, 187, 110, 263; 128/763–765

[56] References Cited

U.S. PATENT DOCUMENTS

| | | | |
|---|---|---|---|
| 4,747,831 | 5/1988 | Kulli | 604/110 |
| 4,758,231 | 7/1988 | Haber et al. | 604/198 |
| 4,838,863 | 6/1989 | Allard et al. | 604/195 X |
| 4,892,107 | 1/1990 | Haber | 128/763 |
| 5,070,885 | 12/1991 | Bonaldo | 128/763 |
| 5,120,311 | 6/1992 | Sagstetter et al. | 604/110 |
| 5,137,521 | 8/1992 | Wilkins | 604/198 |
| 5,374,250 | 12/1994 | Dixon | 128/763 X |
| 5,423,758 | 6/1995 | Shaw | 604/195 X |

*Primary Examiner*—John D. Yasko
*Attorney, Agent, or Firm*—Kenneth H. Johnson; Richard L. Moseley

[57] ABSTRACT

A blood collection device for use with vacuum sample tube is provided having a retractable carrier for a double cannula. A compress spring is mounted between the carrier and the proximal end of the barrel to bias the carrier backward into the barrel. A releasable retaining means is provided to retain the carrier in the proximal end with one end of the double cannula exposed for use. When the retaining means is released the carrier is automatically retracted into the barrel. A cap is provided to cover the original open end and a resealable puncture pad covers the proximal end after the carrier has been retracted.

6 Claims, 2 Drawing Sheets

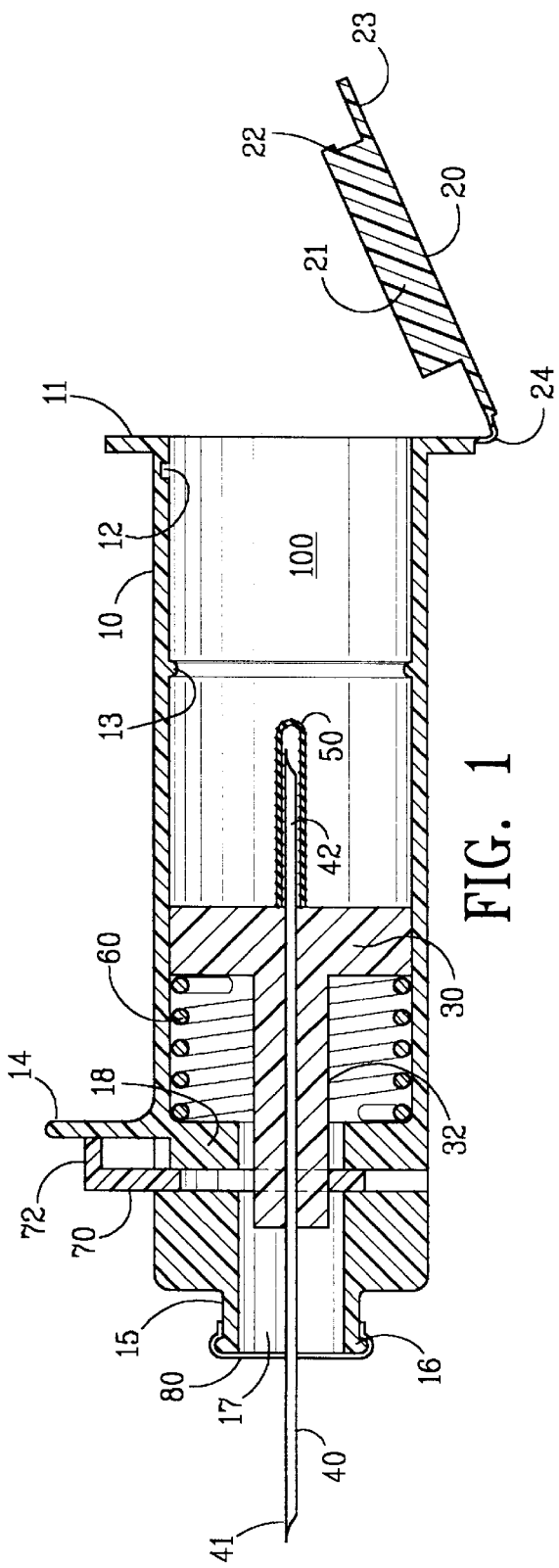
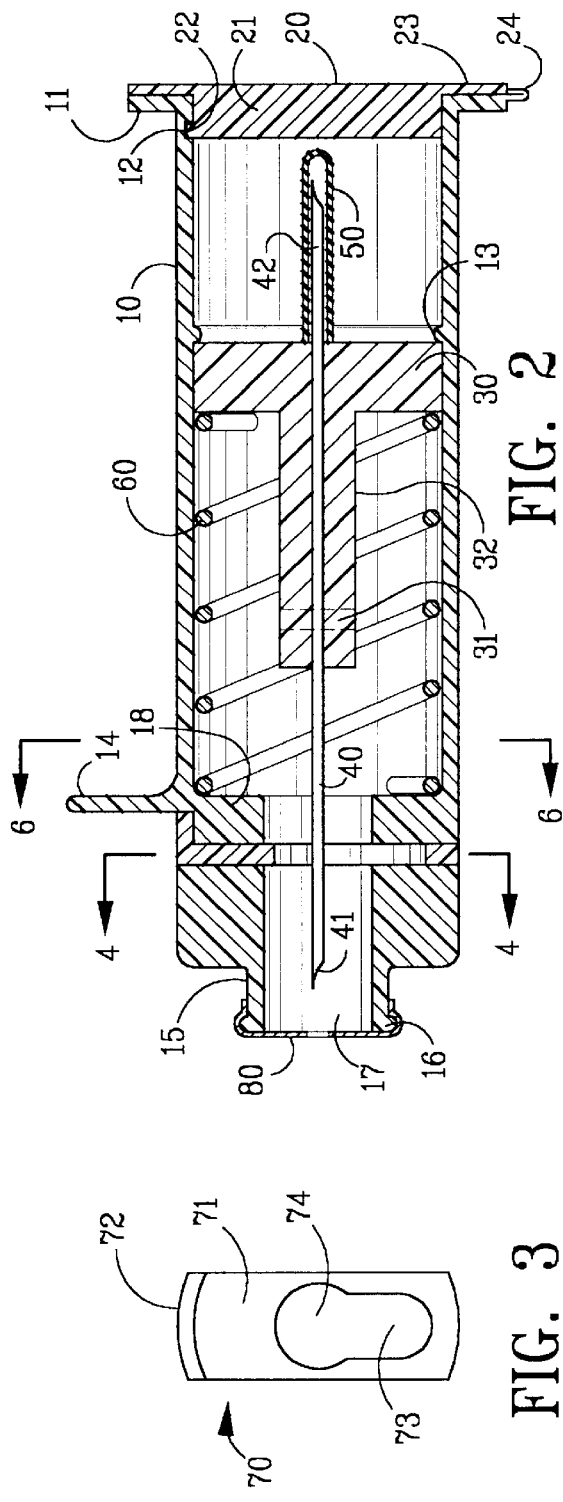
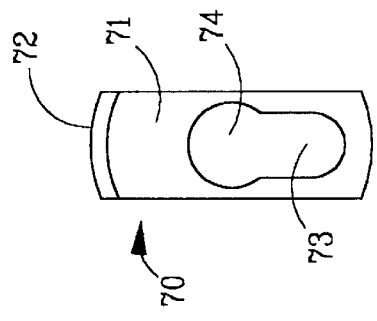

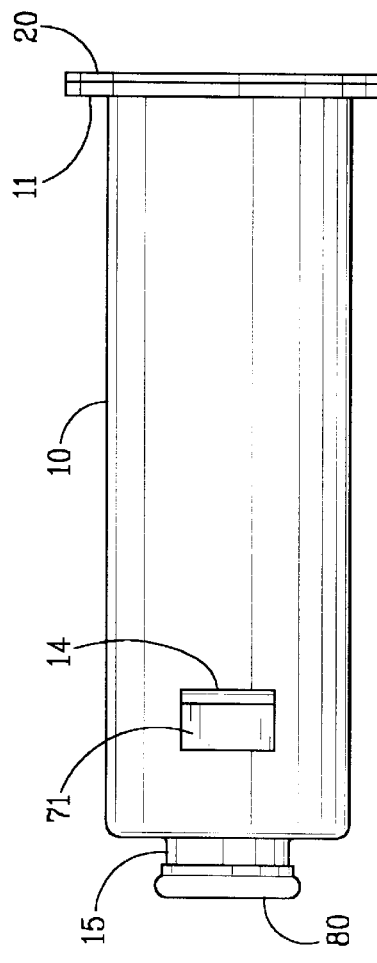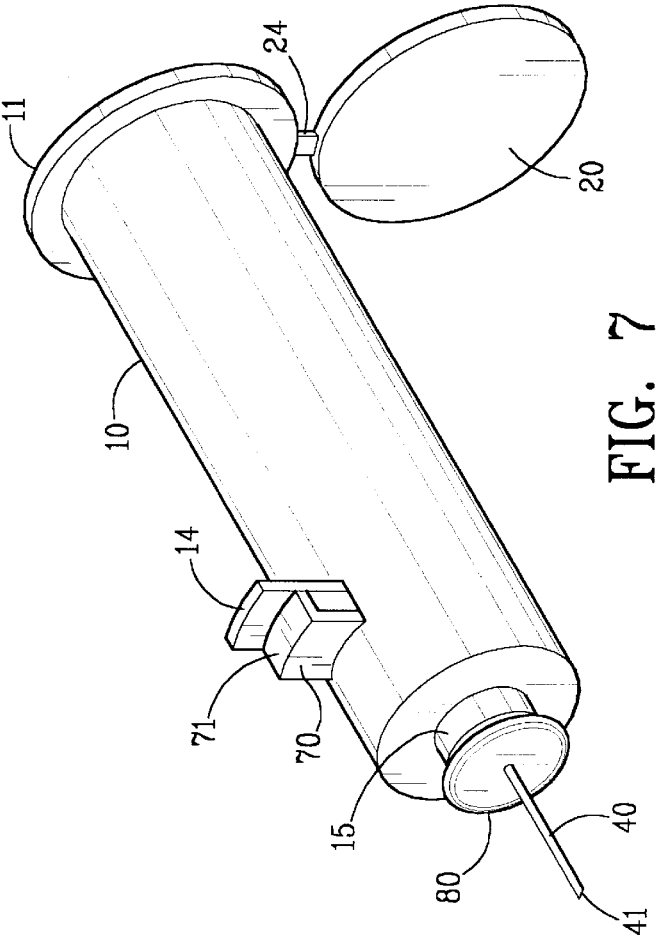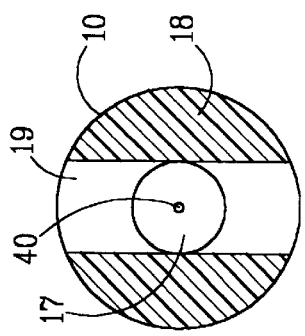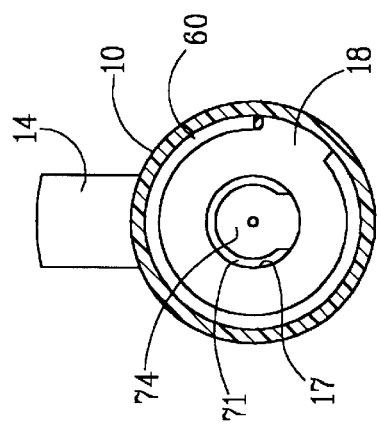

SPRING LOADED RETRACTABLE CANNULA BLOOD DRAWING DEVICE

BACKGROUND OF THE INVENTION

1. Field of the Invention

The present invention relates to devices used to withdraw blood into vacuum tubes for testing. More particularly the invention relates to a device to which a double ended cannula is attached and for receiving the vacuum tube which is pierced by one of the cannula, the other end being inserted into the subject's vein. Most particularly the invention relates to a blood drawing device in which the cannula may be withdrawn into the device and the device closed after use.

2. Related Information

The advent of the AIDS virus has focused attention on diseases which are transmitted by contact with contaminated blood. Many devices are now available on the market to reduce the likelihood of such contact. More particularly there have been devices for retracting the needles of hypodermic syringes into the barrel after use as exemplified in U.S. Pat. Nos. 4,790,822; 4,950,251 and 5,152,750. Additionally the insertion cannula of a catheter has also been made retractable as in U.S. Pat. No. 5,019,049.

Until recently no one has addressed the problem associate with withdrawing blood samples from patients for subsequent testing. The blood drawing device generally consists of cylindrical barrel open at one end and having a double cannula mounted on the end opposite the open end. The double cannula includes two sharp needles mounted together with a passage way connecting the two. One end of the cannula is inserted into the patient's arm and the other, extending into the cylindrical barrel of the blood drawing device, pierces the puncture pad on the end of a blood sample tube. The blood sample tube is generally shipped with a slight vacuum which is sealed inside by the puncture pad. The vacuum assists in drawing the blood into the tube. A typical double cannula is a VACUTAINER BRAND MULTIPLE SAMPLE NEEDLE as manufactured by Becton-Dickson, Inc.

A disposable blood collection device is disclosed in U.S. Pat. No. 5,070,885 in which the double cannula is retractable into the device after use. The retracting mechanism as shown its quite cumbersome requiring a rotation to unlock the cannula carrier which is retracted. Additionally, while a cap is provided to close the open rear end of the device, nothing is provided to cover the opposite end which is left open after the carrier and double cannula have been retracted. In addition the barrel of the blood collection device necessarily includes a slot for the tab that extends outside the barrel for sliding the carrier back into the barrel. This slot can potentially allow blood to leak out.

It is a feature of the present invention that an easily retractable double cannula carrier is provided within a blood collection device while still providing secure retention of the cannula in the use position.

It is a further feature of the present invention that both open ends of the blood collection device are closed after retraction of the cannula.

It is a further feature of the present invention that there is no slot in the barrel for retracting the cannula.

It is a further feature of the present invention that the cannula is retracted automatically.

SUMMARY OF THE INVENTION

To protect against accidental needle prick a blood collection device is provided wherein the double cannula is retractable within the device after all blood samples are taken The device comprises a hollow barrel or tube of semi-rigid plastic material into which the double cannula can be retracted after use. A slidable carrier is provided onto which the double cannula may be mounted. A compressed spring is mounted between the carrier and the proximal end of the barrel to bias the carrier backwardly into the carrier. A releasable retaining means is provided to hold the needle carrier at the proximal end. The needle extends through an opening in the end of the cap which is covered by a puncture pad. When the releasable retaining means is released the compressed spring pushes the needle carrier back up completely into the barrel. The puncture pad seals the opening in the cap. Near the distal end of the barrel an internal ridge is provided to provide a stop for the carrier in the fully retracted position. A cap is provided to cover the distal open end with the puncture pad sealing the proximal end.

BRIEF DESCRIPTION OF THE DRAWING

FIG. 1 is a side elevational view in partial cross section of the blood drawing device showing the double cannula in the exposed position.

FIG. 2 is a side elevational view in partial cross section of the blood drawing device showing the double cannula in the retracted position.

FIG. 3 is a front view of the releasable retaining means used to hold the carrier and cannula at the proximal end.

FIG. 4 is a view taken along line 4—4 in FIG. 2.

FIG. 5 is a top view of the blood collection device with the double cannula in the exposed position.

FIG. 6 is a view taken along line 6—6 in FIG. 2.

FIG. 7 is a perspective view of the blood collection with the double cannula in the exposed position.

DESCRIPTION OF THE PREFERRED EMBODIMENT

For a detailed description of the preferred embodiment the reader is referred to the appended figures in which like components are given like numerals for ease of reference. For reference purposes the term "proximal end" refers to the end of the device from which the exposed cannula extends and the term "distal end" refers to the end into which the blood sample tube is placed.

Referring first to FIG.'s 1 and 2 there is shown an embodiment of the present invention in partial cross section. The invention is shown to comprise a hollow cylindrical barrel 10 having a finger flange 11 for ease of handling at the distal end. The distal end is open while the opposite or proximal end is shown to have a reduced bore 17 through neck 15 and into barrel 10. The narrow neck 15 includes an external ridge 16 at the proximal end about which is secured rubber puncture pad 80. The hollow barrel 10 defines a chamber 100 for receiving a vacuum blood sample drawing tube (not shown). A radially extending tab 14 is provided near the proximal end to protect the releasable means 70 and prevent inadvertent release. Inside the barrel 10 is provided a radially extending ridge 13 which acts as a stop for the carrier when released. The ridge 13 is longitudinally placed such that when the carrier stops in the barrel both the proximal and distal ends of the double cannula are contained within the barrel as shown in FIG. 2. A cap 20 is provided to plug the open distal end of the barrel after use and is attached to the barrel 10 by flexible strap 24. The cap is locked into the closed position by tapered tab 22 which engages internal notch 12 inside of barrel 10.

In the proximal end of the barrel is located needle carrier 30 surrounded by compressed spring 60 which biases the needle carrier inward of the barrel and toward the distal end. Extending through the needle carrier is hypodermic needle 40. The needle 40 extends through the needle carrier 30 to provide a double cannula having a proximal end 41 and distal end 42. A flexible rubber tube 50 surrounds the distal end 42 of the double cannula 40 to prevent blood from escaping into the barrel while inserting the proximal end 41 and before and between sample tube insertions. The end of the needle carrier 30 is passed through the releasable retaining means 70 with the proximal end 41 of the needle extending through bore 17. A rubber puncture pad 15 covers the opening through which the needle is passed.

Referring now to FIG. 3 the releasable retaining means is seen to comprise a small plate 71 having an opening 74 near the top which is slightly larger in diameter than the needle carrier. In addition the plate 71 has a slot 73 extending downward from the opening 74 which is slightly smaller in diameter than the needle carrier and which engages a circumferential groove 31 (seen in FIG. 2) near the proximal end of the needle carrier 30 to hold the needle carrier at the proximal end as shown in FIG. 1. At the top of the plate is a tab 72 which extends distally along the barrel when the plate is placed in the proximal end of the blood drawing device.

FIG. 4 is a view taken along line 4—4 of FIG. 2 and is included for clarity. As shown the barrel 10 is contemplated to be a single molded piece having a reduced internal bore 17 at the proximal end by extending the inner wall radially inwardly as at 18 to provide strength. A slot 19 is provided though the wall 18 to receive the retaining means. FIG. 6 provides further clarity showing the barrel 10 and extended inner wall 18 and tab 14. The retaining means is shown in the depressed position exposing plate 71, opening 74 and top of slot 73.

FIG. 5 is a top view of the blood drawing device in plan view while FIG. 6 is a perspective view of the blood drawing device. In both FIG.'s the proximal end 41 of the double cannula is exposed.

In use the proximal end 41 of the double cannula 40 is inserted into the patient. A vacuum blood sample drawing tube is placed into the chamber 100 and the distal end 42 of the double cannula pierces the rubber over 50 and the stopper of the tube. After the final blood sample has been taken the tab 72 is depressed aligning the opening 74 with the carrier and allowing the spring 60 to push the carrier backward into the barrel until the carrier abuts the ridge 13. The rubber puncture pad 80 is self sealing and seals the proximal end of the device. The cap 20 is then placed over the distal end of the barrel and the entire sealed blood drawing device may be disposed of.

The invention claimed is:

1. A blood collection device comprising
   a hollow cylindrical barrel having a proximal end and a distal end;
   a needle carrier mounted in said proximal end and surrounded by a compressed spring surrounding said carrier which biases said carrier inward of said barrel and toward the distal end of said barrel;
   a releasable retaining means mounted about said needle carrier to retain said needle carrier at the proximal end of said barrel and when released allows said spring to push said needle carrier inward of said barrel and toward the distal end of said barrel;
   a resealable puncture pad covering said proximal end of said barrel; and
   a double cannula mounted on said needle carrier such that the proximal end of said double cannula extends outward of said proximal end of said barrel and through said puncture pad.

2. The blood collection device of claim 1 further comprising a cap to close said distal end.

3. The blood collection device according to claim 1 further comprising means to prevent inadvertent release of said releasable retaining means.

4. The blood collection device according to claim 1 wherein said needle carrier has a circumferential groove near its proximal end and said releasable retaining means comprises
   (i) a plate slidably mounted between said cap and said barrel,
   (ii) a slot in said plate which engages said circumferential groove, and
   (iii) an opening above said slot which is slightly larger in diameter than said needle carrier.

5. The blood collection device according to claim 1 further comprising a radially extending internal ridge in said barrel to stop the rearward movement of said carrier when released.

6. A blood collection device comprising
   a hollow cylindrical barrel having a proximal end and a distal end;
   a slot through said barrel near the proximal end;
   a radially extending internal ridge in said barrel to stop the rearward movement of said carrier when released
   a needle carrier mounted in said proximal end and surrounded by a compressed spring surrounding said carrier which biases said carrier inward of said barrel and toward the distal end of said barrel;
   a circumferential groove near the proximal end of said carrier;
   a releasable retaining means mounted about said needle carrier to retain said needle carrier at the proximal end of said barrel and when released allows said spring to push said needle carrier inward of said barrel and toward the distal end of said barrel said retaining means comprising,
   (i) a plate slidably mounted in said slot,
   (ii) a second slot in said plate which engages said circumferential groove, and
   (iii) an opening above said second slot which is slightly larger in diameter than said needle carrier;
   a resealable puncture pad covering said proximal end of said barrel; and
   a double cannula mounted on said needle carrier such that the proximal end of said double cannula extends outward of said proximal end of said barrel and through said puncture pad.

* * * * *